United States Patent [19]
Froot

[11] 4,087,685
[45] May 2, 1978

[54] FLUORESCENT MICROANALYTICAL SYSTEM AND METHOD FOR DETECTING AND IDENTIFYING ORGANIC MATERIALS

[75] Inventor: Howard Arthur Froot, Hopewell Junction, N.Y.

[73] Assignee: International Business Machines Corporation, Armonk, N.Y.

[21] Appl. No.: 758,516

[22] Filed: Jan. 11, 1977

[51] Int. Cl.$^2$ .............................................. G09K 3/00
[52] U.S. Cl. .................................. 250/302; 250/461 R
[58] Field of Search ............................ 250/302, 461 R

[56] References Cited
U.S. PATENT DOCUMENTS

| | | | |
|---|---|---|---|
| 3,774,030 | 11/1973 | O'Connor et al. | 250/302 |
| 3,939,350 | 2/1976 | Kronick et al. | 250/302 X |

Primary Examiner—Davis L. Willis
Attorney, Agent, or Firm—Edward W. Brown

[57] ABSTRACT

A rapid, non-destructive system and method for insitu detection and identification of luminescent organic particulates or films on non-luminescent devices, such as semiconductor wafers and chips. The major optical components of the system comprises a luminescent vertical illuminator, an image device and a detector. The method is based on the principle that a very large number of organic materials luminesce when excited by ultraviolet radiation. By scanning the luminescent emission spectra of the known organic materials used in manufacture, a characteristic curve of intensity versus wavelength is obtained and matched to curves of known organic materials, thereby permitting detection and identification of the particulates.

10 Claims, 4 Drawing Figures 4,087,685

FLUORESCENT MICROANALYTICAL SYSTEM AND METHOD FOR DETECTING AND IDENTIFYING ORGANIC MATERIALS

BACKGROUND OF THE INVENTION

This invention relates to a system and method for detection and identification of luminescent organic particulates or films on devices and, more particularly, to the detection and/or identification of these particulates or films during the manufacture of semiconductor devices.

A major problem in the manufacture of semiconductor devices has always been the presence of extraneous particulate matter in active areas. These have caused defects affecting yields, reliability and performance.

In the past, each semiconductor chip contained only one or, at most, two active devices and thus required large scale production of identical chips. The active geometries were fairly large and only occupied a small portion of the available area or commonly called real estate of a chip. Defect-causing particles were in the hundredths of a millimeter size range and the probability of their being in a critical region was low. In addition, while the cost per circuit was relatively high, the cost per chip was not. Because of all these factors, the economic impact of particulates was not very great.

Today, the dimensions of the active devices have been reduced and their number per chip have been increased by orders of magnitude thereby increasing the useable real estate on a chip by multilevel interconnections of narrower conductors. The production of these large scale integrated (LSI) chips is small relative to the past single device to the large scale production of many small volume chips and, while the cost per device or circuit has been drastically reduced, the cost per chip has increased sharply. Accordingly, the economic impact of defects caused by particulate contamination has become significant because a particle as small as a submicron can make an entire chip unuseable.

In some cases, the mere detection of the particulates during manufacturing is sufficient so as to monitor the contaminate level and if it exceeds a certain level to stop the manufacturing lines. In other cases, this detection must be followed by an identification of the particulate material so that its source may be found and proper corrective actions instituted to prevent its reoccurrence.

While a number of detection systems and analytical tools are available, they do not permit either on-line detection and identification or organic particles or film or even rapid off-line identification. In addition, the analytical tools require a destructive test.

BRIEF DESCRIPTION OF THE INVENITON

It is an object of the present invention is to provide a detection and identification system and method for rapidly detecting luminescent organic particulates or films without destroying the substrate or device on which they are carried.

It is a further object of the invention to provide a detection system and method which permits on-line monitoring of luminescent organic contaminants during manufacturing and the ability to stop manufacturing if the contaminates reach a predetermined level.

Another object of the invention is to provide an identification system and method which allows, during manufacture, either on-line or rapid off-line identification or specific ones of a number of organic luminescent materials known to have been introduced during some stage of the manufacture process, but have become contaminants at a later stage of the process.

In general, the foregoing and other objects of the present invention is a system and method comprising means for and the steps of detecting and identifying organic luminescent material as small as submicron carried or embedded in a device by exposing the substrate to electromagnetic radiation of sufficient energy to cause the organic material to luminesce, detecting the luminescent emission spectra of the organic materials, and comparing the spectra with known spectra of organic materials used in the manufacturing process to identify one or more of the luminescent materials.

In the preferred embodiment of the present invention, the system and method is designed to identify specific organic luminescent materials which are known to be used in the manufacturing process but are showing up in stages of the process where they should not be present. In the present instance, the emission spectra of the known materials are stored in a computer and as the spectra of the materials on the device are detected and generated, the generated spectra are compared with all of the stored spectra until a one-on-one match is obtained, thereby identifying the specific material. This embodiment can either be carried out on-line or off-line.

In another embodiment of the invention, the system and method is designed to monitor the contaminant level of the organic luminescent materials known to be used in process so as to be able to maintain the contaminant level at a predetermined level. Herein, the system is inserted in the some stages of the manufacturing line with the emission spectra of the known organic materials used in a earlier stage of the line stored in the computer. A predetermined number of these contaminant particles/unit area is set in the computer and the devices are scanned by the system and the number of contaminant particles/unit area are counted and compared with the predetermined number. If the detected number exceeds the predetermined number, a visual indication is given so that corrective action can be taken.

DESCRIPTION OF THE PREFERRED EMBODIMENTS OF THE INVENTION

The majority of organic luminescent materials absorb in the ultraviolet wavelengths of the electromagnetic spectrum and, because the molecules possess a series of closely spaced energy levels and can go from a lower to a higher energy level by the absorption of a discrete quantum of radiation equal in energy to the difference between the two energy states, the re-emission of this energy when the molecules return to its lower energy level is called luminescence and usually is in the visible portion of the electromagnetic spectrum. Among the organic materials which luminesce, the most intensely luminescent are the aromatic hydrocarbons, followed by the heteroaromatic and aromatic carbonyl compounds, the conjugated aliphatics, and the very weakly fluorescent saturated aliphatics.

In organic molecules, the electrons move in polycentric orbitals called molecular orbitals. Each orbital has quantum numbers associated with it with electrons added to orbitals in order of increasing energy and according to Pauli principle. A state for a molecule is determined by this orbital electronic configuration with no two materials having molecules with exactly the same energy pattern. Therefore, no two organic materials will have exactly the same emission peaks. In addition, no two organic materials will have exactly the same intensity relationship between peaks. Because of this, each material will have a unique emission spectrum.

The population of solid organic materials which become contaminants in a manufacturing process, herein semiconductor manufacturing, usually will be less than one hundred different materials. This makes identification of the emission spectrum of these materials very practical.

Figure 1:
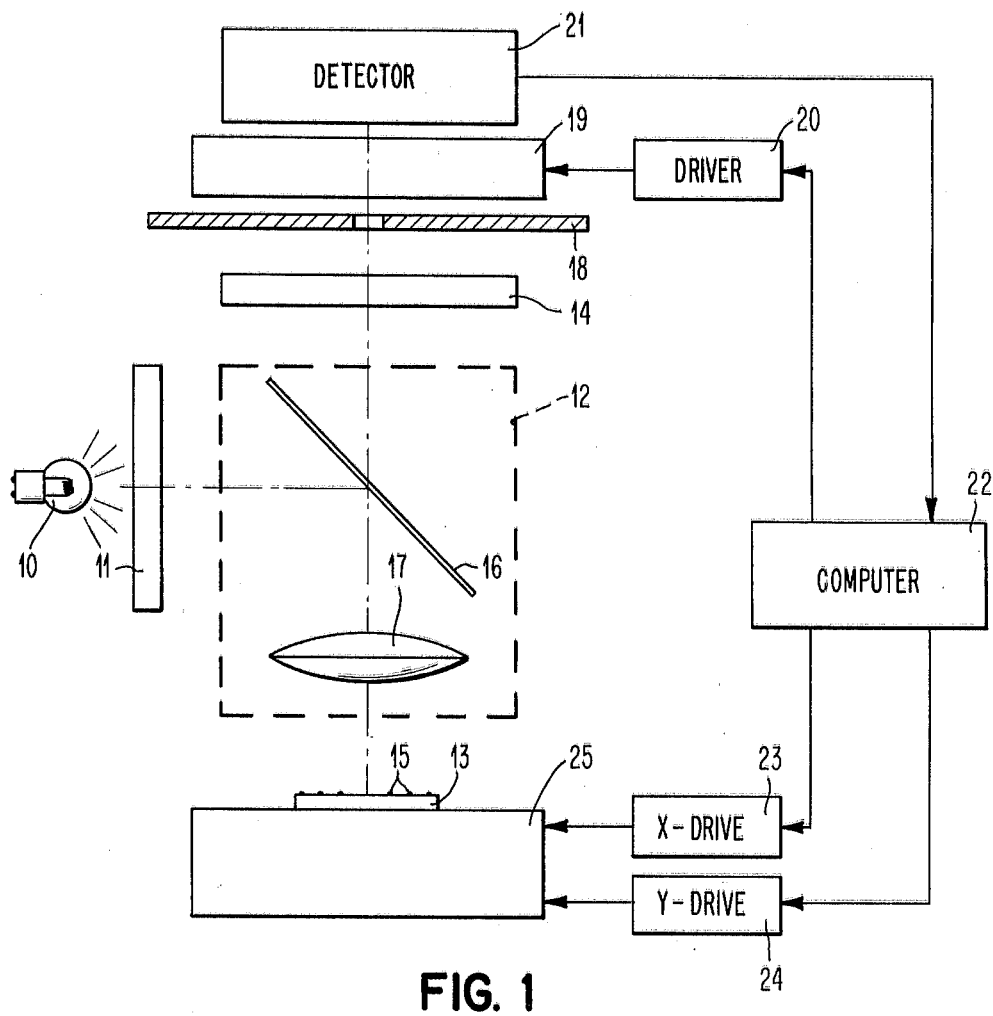
FIG. 1 is a schematic block diagram illustrating the preferred embodiment of the system and method of the present invention.

In FIG. 1, the system of the present invention is illustrated and includes a luminescent vertical illuminator including a ultraviolet light source 10, a selection filter 11 to limit the wavelengths of the source to 2000 to 4000 A, an imaging device 12 to deflect the ultraviolet light onto a device 13, and a suppression filter 14, such as a BG 38 red, to block any light shorter than 4000 A while passing all longer wavelengths emitted from organic materials 15 on the device 13.

Herein, the light source 10 is a Xenon lamp emitting high intensity broad band ultraviolet light and, preferably, is a XBO 150. The imaging device 12 comprises a high efficiency beam splitter 16 for deflecting the ultraviolet light through a lens 17 onto the substrate 13. In the present instance, a dichroic beam splitter is utilized and matched to the selection filter 11 which not only reflects the ultraviolet light 90° onto the device but transmits any visible light through the beam splitter to a light trap, if desired. The visible light emitted from the organic particles 15 on the device 13 will be transmitted through the beam splitter for detection and any ultraviolet light will be reflected 90° to the ultraviolet light source. Because the intensity of the light emitted from the device 13 is directly proportional to the fourth power of the numerical aperture, and inversely proportional to the square of the total magnification, moderate low magnification objective lens, such as APO 254/0.65 n.a., is desired. Of course, the lens 17 used should not contain any autoluminescing components To limit the emitting light or signal to a particular area, a variable measuring diaphragm 18 is positioned in the path of the emitted light above the suppression filter. Herein, the diaphragm can be stopped down to a $0.5\mu \times 0.5\mu$ square. A diaphragm variable down to this submicron size is particularly important when more than one luminescent particulate is in the field view on the device 13.

Positioned above the diaphragm is a scanning monochromater 19, which, herein, is a Schoeffel GM100 grating monochromator with a driver 20 including a stepping motor (not shown) attached to the drive shaft (not shown). After passing through the monochromator 19, the emitted visible light is received by a detector 21 which, in the present instant, is a S-20 type photo-multiplier tube. The monochromator 19 is stepped from 4000 to 7000 A in 5 A steps under control of an IBM 5100 computer 22. At each step of the monochromator, one hundred separate intensity readings from the detector 21 are averaged and stored in the computer 22. Simultaneously, the wavelength is determined by the voltage of a linear potentiometer attached to the monochromator drive shaft and also stored.

In the fully automated mode of the present system, the computer controls an 'X' drive 23 and 'Y' drive 24 to step the device stage 25 in a meander pattern so that the entire sample is scanned. The stage is stopped whenever a signal is received at the detector 21. This indicates that a luminescent particle is in the field of view. The monochromator is then scanned, the results analyzed and outputted according to the APL algorithm programmed in the computer and given below:

Datan ← Data ÷ Norm

Compare ← (Store A. = Datan)/τ1 ↑ ρ Store

Match ← Name [Compare]

Match wherein:
Data = Spectral emission data from unknown material
Norm = Stored data to normalize for system response
Store = $x$ by 600 matrix of normalized emission data for known materials.
Name = Stored name list of known materials in "store".

If desired, the computer 22 can be programmed using state of the art techniques to drive a plotter to plot the intensity versus wavelength curves of the detected luminescent organic materials. The comparison is then made visually between the plotted curves and the known curves.

Figure 2A:
FIG. 2A is a cross-section of a substrate carrying organic luminescent particles.
Figure 2B:
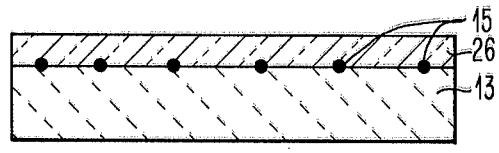
FIG. 2B is a cross-section of a substrate having a layer transparent to the emission wavelengths of the organic particles with the particles being between the substrate and the layer.

FIGS. 2A and 2B show two devices 13 enlarged from FIG. 1 carrying luminescent organic particles 15. In FIG. 2B, the contaminating particles are covered by a layer 26 as part of the manufacturing process. When the layer 26 is transparent to the emitting light, such as by being $SiO_2$, the system and method of the present invention can be used to detect these contaminants.

Figure 3:
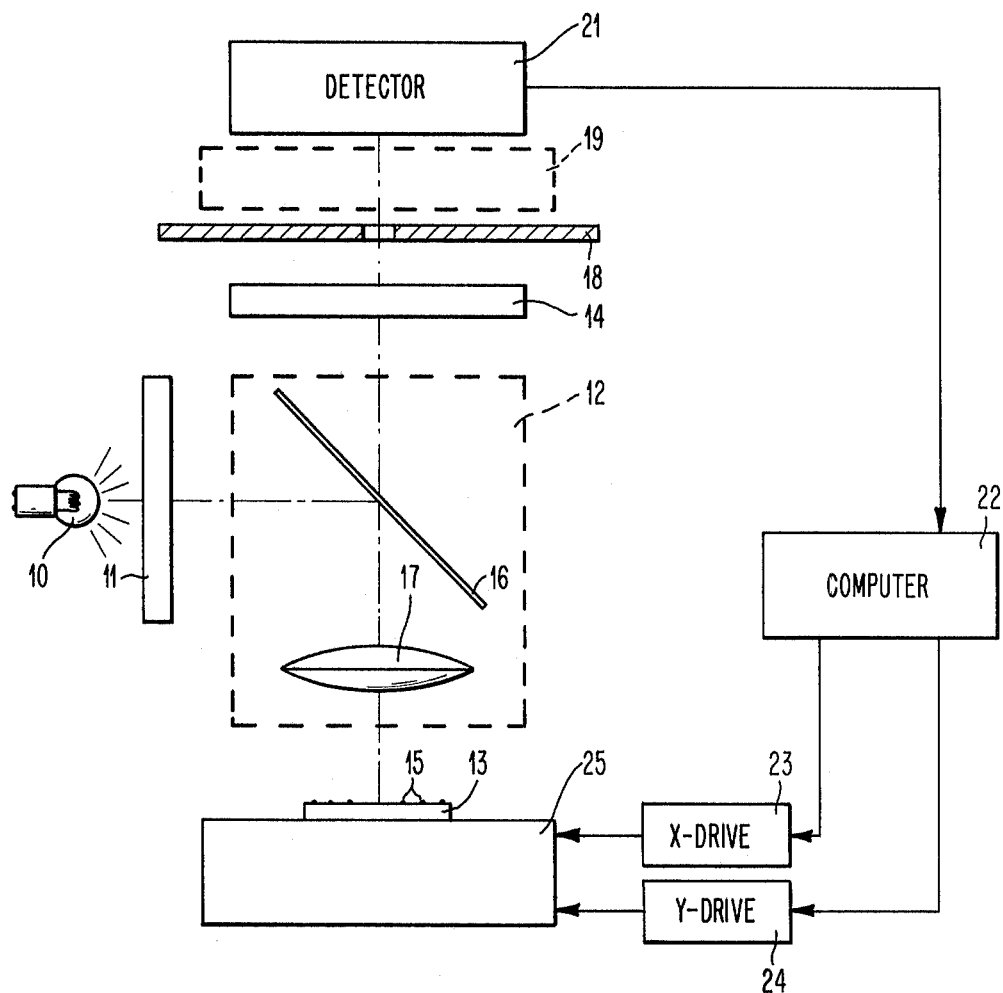
FIG. 3 is a schematic block diagram illustrating another embodiment of the system and method of the present invention.

In FIG. 3, the system of FIG. 1 has been modified to be used on the manufacturing line to monitor a predetermined level of contaminants. In this embodiment, the luminescent organic particles are not identified, but only counted so that the scanning monochromater is not necessary. Herein, the predetermined level of luminescent contaminants/unit area are stored in the computer 22 which also controls the movable stage 25 to permit the exposing light to scan the device. The emitting light signals from different particles/scanned unit area are detected and counted by the computer. If this number exceeds the predetermined stored number, a warning signal is given. In this embodiment, it is not necessary for the luminescent organic particles to be known inasmuch as the particles are not to be identified, but only detected and counted.

While the invention has been particularly described with reference to specific embodiments thereof, it will be understood by those skilled in the art that various changes may be made therein without departing from the spirit and scope of the invention.

What is claimed is:

1. A system for detecting possible contaminating organic luminescent materials carried on or embedded in a device under manufacture, said materials having been used in the manufacture and having known luminescent emission spectra, said system comprising;

means for exposing the device to electromagnetic radiation of sufficient energy to cause the organic materials with the known emission spectra to luminesce;

means for detecting luminescent emission spectra emanating from the device as a result of the exposure; and means for comparing said emission spectra with the known emission spectra of the organic materials used in manufacture thereby detecting whether any one of these materials are contaminating said device.

2. The system of claim 1 wherein said system includes computer means for storing said known emission spectra and automatically comparing the stored emission spectra with those detected from said device.

3. The system of claim 1 wherein said detection system includes means for scanning said field of exposure at a rapid rate so as to provide data for intensity versus wavelength curves, whereby a comparison can be made with known intensity versus wavelength curves of said organic materials.

4. The system of claim 1 wherein said system further includes a bidirectional movable stage so as to permit scanning of the device with the exposing radiation.

5. The system of claim 4 wherein said stage is automatically stopped once luminescence is detected.

6. The system of claim 2 wherein said detected spectra are compared with all the stored spectra until a one-on-one match is obtained, thereby identifying the specific material.

7. A method of detecting possible contaminating organic luminescent materials carried on or embedded in a device under manufacture, said materials having been used in the manufacture and having luminescent emission spectra, said method comprising the steps of:

exposing the device to electromagnetic radiation of sufficient energy to cause the organic materials to luminesce; and detecting luminescent emission spectra emanating from the device as a result of the exposure so as to identify the level of contaminating material carried on or embedded in the device.

8. The method of claim 7 wherein said luminescent emission spectra are known, and said method further includes comparing said emission spectra with the known emission spectra of the organic materials used in manufacture thereby identifying whether anyone of these materials are contaminating said device.

9. The method of claim 8 wherein a contaminant level/unit area of luminescent organic materials is predetermined and said comparison is made with said predetermined level without concern to identification of specific materials, thereby permiting continuous monitoring of the contaminant level.

10. The method of claim 7 wherein said device is scanned with the exposing radiation, but once emitted luminescence is detected, the exposure scanning is stopped and the emitted luminescence is optically scanned so as to determine its characteristic curve as to intensity and wavelength.

* * * * *